(12) United States Patent
Wang et al.

(10) Patent No.: US 10,188,728 B2
(45) Date of Patent: Jan. 29, 2019

(54) COMPOSITIONS AND METHODS FOR TREATMENT OF CANCER

(71) Applicant: TEMPLE UNIVERSITY—OF THE COMMONWEALTH SYSTEM OF HIGHER EDUCATION, Philadelphia, PA (US)

(72) Inventors: Bin Wang, Thornton, PA (US); Mohammad F. Kiani, Wynnewood, PA (US); Yuan Tang, Elkins Park, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 129 days.

(21) Appl. No.: 14/650,355

(22) PCT Filed: Oct. 16, 2013

(86) PCT No.: PCT/US2013/065164
§ 371 (c)(1),
(2) Date: Jun. 8, 2015

(87) PCT Pub. No.: WO2014/092858
PCT Pub. Date: Jun. 19, 2014

(65) Prior Publication Data
US 2015/0366993 A1    Dec. 24, 2015

Related U.S. Application Data

(60) Provisional application No. 61/736,230, filed on Dec. 12, 2012.

(51) Int. Cl.
*A61K 9/127* (2006.01)
*A61K 39/395* (2006.01)
(Continued)

(52) U.S. Cl.
CPC ........ *A61K 39/3955* (2013.01); *A61K 9/1271* (2013.01); *A61K 9/1273* (2013.01);
(Continued)

(58) Field of Classification Search
CPC .................................................... A61K 9/1271
See application file for complete search history.

(56) References Cited

U.S. PATENT DOCUMENTS

| | | |
|---|---|---|
| 4,753,788 A | 6/1988 | Gamble |
| 5,013,556 A | 5/1991 | Woodle et al. |

(Continued)

FOREIGN PATENT DOCUMENTS

WO    2011133617 A1    10/2011

OTHER PUBLICATIONS

Wu et al, "Reversal of Multidrug Resistance by Transferrin-Conjugated Liposomes Co-encapsulating Doxorubicin and Verapamil" J Pharm Pharmaceut Sci, 10(3):350-357 (2007).

(Continued)

*Primary Examiner* — Benjamin J Packard
(74) *Attorney, Agent, or Firm* — Drinker Biddle & Reath LLP (57) ABSTRACT

Provided are compositions, methods and kits for treating cancer comprising targeted liposomes comprising a chemotherapy agent and a sensitizer for the chemotherapy agent, and non-targeted liposomes comprising an anti-angiogenic agent. In some embodiments, the targeted liposomes are immunoliposomes. In further embodiments, the immunoliposomes bind to Her-2/neu, and the composition is for treating breast cancer.

26 Claims, 2 Drawing Sheets

(51) Int. Cl.

| | | |
|---|---|---|
| C07K 16/22 | (2006.01) | |
| C07K 16/32 | (2006.01) | |
| A61K 45/06 | (2006.01) | |
| A61K 31/277 | (2006.01) | |
| A61K 31/704 | (2006.01) | |
| A61K 47/69 | (2017.01) | |
| A61K 39/00 | (2006.01) | |

(52) U.S. Cl.
CPC .......... *A61K 31/277* (2013.01); *A61K 31/704* (2013.01); *A61K 45/06* (2013.01); *A61K 47/6913* (2017.08); *A61K 47/6915* (2017.08); *C07K 16/22* (2013.01); *C07K 16/32* (2013.01); *A61K 2039/507* (2013.01); *C07K 2317/24* (2013.01)

(56) References Cited

U.S. PATENT DOCUMENTS

| | | |
|---|---|---|
| 5,192,549 A | 3/1993 | Barenolz et al. |
| 5,316,771 A | 5/1994 | Barenholz et al. |
| 5,395,619 A | 3/1995 | Zalipsky et al. |
| 5,527,528 A | 6/1996 | Allen et al. |
| 5,631,018 A | 5/1997 | Zalipsky et al. |
| 6,146,659 A | 11/2000 | Rahman |
| 6,740,335 B1 | 5/2004 | Moynihan et al. |
| 7,122,202 B2 | 10/2006 | Allen et al. |
| 8,241,663 B2 | 8/2012 | Isozaki et al. |
| 2006/0067998 A1 | 3/2006 | Kurzrock et al. |
| 2006/0159736 A1 | 7/2006 | Zalipsky et al. |
| 2009/0162425 A1 | 6/2009 | Divi et al. |
| 2020/0239652 | 9/2010 | Rochiltz et al. |
| 2010/0254914 A1 | 10/2010 | Park et al. |
| 2010/0260677 A1 | 10/2010 | Bhatia et al. |
| 2011/0081404 A1 | 4/2011 | Okada et al. |
| 2011/0159080 A1 | 6/2011 | Lowery |
| 2012/0135064 A1 | 5/2012 | Campbell |
| 2012/0294931 A1 | 11/2012 | Kim et al. |
| 2013/0101666 A1 | 4/2013 | Park et al. |

OTHER PUBLICATIONS

Abrishami, et al, "Preparation, Characterization, and In Vivo Evaluation of Nanoliposomes-Encapsulated Bevacizumab (Avastin) for Intravitreal Administration" Retina, 29(5):699-703 (2009).
Yardley, "Integrating Bevacizumab Into the Treatment of Patients With Early-Stage Breast Cancer: Focus on Cardiac Safety" Clinical Breast Cancer, 10(2):119-129 (2010).
Shmeeda, et al, "Her2-targeted pegylated liposomal doxorubicin: Retention of target-specific binding and cytotoxicity after in vivo passage" Journal of Controlled Release, 136(2):155-160 (2009).
Fang et al, "The EPR effect: Unique features of tumor blood vessels for drug delivery, factors involved, and limitations and augmentation of the effect" Advanced Drug Delivery Reviews, 63(3):136-151 (2011).
Rosano et al, "Targeted Delivery of VEGF after a Myocardial Infarction Reduces Collagen Deposition and Improves Cardiac Function" Cardiovasc Eng Technol., 3(2):237-247 (Jun. 2012).
Wang et al, "In Vitro Cytotoxicity of Stealth Liposomes Co-encapsulating Doxorubicin and Verapamil on Doxorubicin-Resistant Tumor Cells" Biol. Pharm. Bull., 28(5):822-828 (2005).
Wedam et al, "Antiangiogenic and Antitumor Effects of Bevacizumab in Patients With Inflammatory and Locally Advanced Breast Cancer" Journal of Clinical Oncology, 24(5):769-777 (2006).
Lee, "Polymer-Dual Drug Conjugates Targeted to Her2 Overexpressing Breast Cancer" PhD Thesis May 4, 2012. [Retrieved from the internet Dec. 22, 2013: <https:archive.hshsl.umaryland.edu/bitstream/10713/1685/1/Lee_umaryland_0373D_10287.pdf>].
Okuda, et al, "Multidrug Delivery Systems with Single Formulation" Journal of Biomaterials and Nanobiotechnology, 3:50-60 (Jan. 2012).

Hare et al, "Targeting combinations of liposomal drugs to both tumor vasculature cells and tumor cells for the treatment of HER2-positive breast cancer" Journal of Drug Targeting, Epub Oct. 8, 2012, 21(1):87-96 (2012).
Allen, et al, "Liposomal drug delivery systems: From concept to clinical applications" Advanced Drug Delivery Reviews, Epub Oct. 1, 2012, 65(1):36-48 (2013).
Aghajanian et al, "OCEANS: A Randomized, Double-Blind, Placebo-Controlled Phase III Trial of Chemotherapy With or Without Bevacizumab in Patients With Platinum-Sensitive Recurrent Epithelial Ovarian, Primary Peritoneal, or Fallopian Tube Cancer" Journal of Clinical Oncology, Epub Apr. 23, 2012, 30(17):2039-2045 (Jun. 10, 2012).
Del Carmen, et al, "A phase II clinical trial of pegylated liposomal doxorubicin and carboplatin plus bevacizumab in patients with platinum-sensitive recurrent ovarian, fallopian tube, or primary peritoneal cancer" Gynecologic Oncology, Epub May 30, 2012, 126(3):369-374 (2012).
Labidi et al, "Bevacizumab and Paclitaxel for Breast Cancer Patients with Central Nervous System Metastases: A Case Series" Clinical Breast Cancer, 9(2):118-121 (2009).
Rochlitz et al, "Combination of bevacizumab and 2-weekly pegylated liposomal doxorubicin as first-line therapy for locally recurrent or metastatic breast cancer. A multicenter, single-arm phase II trial (SAKK 24/06)" Annals of Oncology, 22(1):80-85 (2011).
Verschraegen et al, "Phase II study of bevacizumab with liposomal doxorubicin for patients with platinum- and taxane-resistant ovarian cancer" Annals of Oncology, Epub Jul. 31, 2012, 23(12):3104-3110 (2012).
Stevenson et al, "Bevacizumab and breast cancer: what does the future hold?" Future Oncol., 8(4):403-414 (Apr. 2012).
Koutras et al, "Bevacizumab in the treatment of breast cancer" Cancer Treatment Reviews, 36(1):75-82 (2010).
Lohmann et al, "Patients With Metastatic Breast Cancer Using Bevacizumab as a Treatment: Is There Still a Role for it?" Current Treatment Options in Oncology, 13(2):249-262 (Jun. 2012).
Coyne et al, "Epirubicin-[Anti-HER2/neu] Synthesized with an Epirubicin-(C13-imino)-EMCS Analog: Anti-Neoplastic Activity against Chemotherapeutic-Resistant SKBr-3 Mammary Carcinoma in Combination with Organic Selenium" Journal of Cancer Therapy, 2:22-39 (2011).
ClinicalTrials NCT01367028, "Multicentre Randomized Phase II Study of Neoadjuvant Trastuzumab Plus Docetaxel With and Without Bevacizumab and Trastuzumab Plus Docetaxel Plus Non-pegylated Liposome-encapsulated Doxorubicin (NPLD) With and Without Bevacizumab in HER2-positive Early Breast Cancer" Nov. 28, 2012. [Retrieved from the Internet Dec. 23, 2013: <http://clinicaltrials.gov/archive/NCT01367028/2012_11_28].
Dhillon, "Bevacizumab Combination Therapy" Drugs, 72(7):917-930 (2012).
Park et al, "Anti-HER2 Immunoliposomes: Enhanced Efficacy Attributable to Targeted Delivery" Clinical Cancer Research, 8:1172-1181 (2002).
Scott et al, "Targeting VEGF-encapsulated immunoliposomes to MI heart improves vascularity and cardiac function" The FASEB Journal, 23:3361-3367 (2009).
Ranson et al, "Treatment of advanced breast cancer with sterically stabilized liposomal doxorubicin: results of a multicenter phase II trial" Journal of Clinical Oncology, 15(10):3185-3191 (Oct. 1, 1997).
Northfelt et al, "Pegylated-liposomal doxorubicin versus doxorubicin, bleomycin, and vincristine in the treatment of AIDS-related Kaposi's sarcoma: results of a randomized phase III clinical trial" Journal of Clinical Oncology, 16(7):2445-2451 (Jul. 1, 1998).
Gordon et al, "Recurrent Epithelial Ovarian Carcinoma: A Randomized Phase III Study of Pegylated Liposomal Doxorubicin Versus Topotecan" Journal of Clinical Oncology, 19(14):3312-3322 (Jul. 15, 2001).
Alexopoulos et al, "Phase II study of pegylated liposomal doxorubicin (Caelyx) and docetaxel as first-line treatment in metastatic breast cancer" Annals of Oncology, 15:891-895 (2004).

(56) References Cited

OTHER PUBLICATIONS

Naturforsch, "Modulation of Anticancer Drug-Induced P-Glycoprotein Expression by Naringin" (M. M. Ali et al, Effect of Naringin on Multidrug Resistance), 64c:109-116 (2009).
Zalipsky, "Synthesis of an End-Group Functionalized Polyethylene Glycol-Lipid Conjugate for Preparation of Polymer-Grafted Liposomes" Bioconjugate Chem., 4(4):296-299 (1993).
Zalipsky et al, "Long circulating, cationic liposomes containing amino-PEG-phosphatidylethanolamine" FEBS Letters, 353:71-74 (1994).
Zalipsky et al, "Peptide Attachment to Extremities of Liposomal Surface Grafted PEG Chains: Preparation of the Long-Circulating Form of Laminin Pentapeptide, YIGSR" Bioconjugate Chem., 6(6):705-708 (1995).
Nallamothu et al, "A Tumor Vasculature Targeted Liposome Delivery System for Combretastatin A4: Design, Characterization, and In Vitro Evaluation" AAPS Pharm Sci Tech, 7(2):E1-E10 (2006).
Hurwitz et al, "Bevacizumab Irinotecan, Fluorouracil, and Leucovorin for Metastatic Colorectal Cancer" The New England Journal of Medicine, 350(23):2335-2342 (Jun. 3, 2004).
Kirpotin et al, "Sterically Stabilized Anti-HER2 Immunoliposomes: Design and Targeting to Human Breast Cancer Cells in Vitro" Biochemistry, 36(1):66-75 (1997).
Park et al, "Development of anti-p185HER2 immunoliposomes for cancer therapy" Proc. Natl. Acad. Sci. 92:1327-1331 (Feb. 1995).
Al-Batran et al, "The clinical benefit of pegylated liposomal doxorubicin in patients with metastatic breast cancer previously treated with conventional anthracyclines: a multicentre phase II trial" British Journal of Cancer, 94(11):1615-1620 (2006).
Mamot et al, "Epidermal growth factor receptor-targeted immunoliposomes significantly enhance the efficacy of multiple anticancer drugs in vivo" Cancer Res. 65(24):11631-11638 (Dec. 15, 2005).
Pattillo et al, "Targeting of the Antivascular Drug Combretastatin to Irradiated Tumors Results in Tumor Growth Delay" Pharmaceutical Research, 22(7):1117-1120 (Jul. 2005).
Moghimi et al, "Long-Circulating and Target-Specific Nanoparticles: Theory to Practice" Pharmacological Reviews, 53(2):283-318 (2001).
Lasic et al, "Sterically stabilized liposomes in cancer therapy and gene delivery" Current Opinion in Molecular Therapeutics, 1(2):177-185 (1999).
Lian et al, "Trends and Developments in Liposome Drug Delivery Systems" Journal of Pharmaceutical Sciences, 90(6):667-680 (Jun. 2001).
Chia et al, "Pegylated Liposomal Doxorubicin and Trastuzumab in HER-2 Overexpressing Metastatic Breast Cancer: A Multicenter Phase II Trial" Journal of Clinical Oncology, 24(18):2773-2778 (Jun. 20, 2006).
Park et al, "Tumor targeting using anti-her2 immunoliposomes" Journal of Controlled Release, 74:95-113 (2001).
Yang et al, "Preparation and evaluation of paclitaxel-loaded PEGylated immunoliposome" Journal of Controlled Release, 120:169-177 (2007).
Jones et al, "Clinical and pathological absence of cardiotoxicity after liposomal doxorubicin" The Lancet Oncology, 5:575-577 (Sep. 2004).
Maeda et al, "Vascular permeability enhancement in solid tumor: variious factors, mechanisms involved and its implications" International Immunopharmacology, 3:319-328 (2003).
Derksen et al, "An improved method for the covalent coupling of proteins to liposomes" Biochimica et Biophysica Acta, 814:151-155 (1985).
Tang et al, "Targeted Multidrug Delivery System for Overcoming Chemoresistance in Breast Cancer" Biomedical Engineering Society 2012 Annual Meeting in Atlanta, Georgia, USA, Poster P-Th-A-239 (Oct. 25, 2012).
Tang et al., "Targeted multidrug delivery system to overcome chemoresistance in breast cancer," International Journal of Nanomedicine, vol. 12, pp. 671-681, 2017.
Allen et all, "A new strategy for attachment of antibodies to sterically stabilized liposomes resulting in efficient targeting to cancer cells" Biochimica et Biophysica Acta, 1237:99-108 (1995).
Lasic, "Doxorubicin in sterically stabilized liposomes" Nature, 380:561-566 (Apr. 11, 1996).
Information Search Report and Written Opinion of the International Searching Authority, dated Jan. 23, 2014.
International Preliminary Report on Patentability, dated Jun. 16, 2015.

COMPOSITIONS AND METHODS FOR TREATMENT OF CANCER

CROSS-REFERENCE TO RELATED APPLICATION

The benefit of the filing date of U.S. Provisional Patent Application No. 61/736,230, filed Dec. 12, 2012, is hereby claimed. The entire disclosure of the aforesaid application is incorporated herein by reference.

FIELD OF THE INVENTION

The present invention relates to compositions and methods for the treatment of cancer.

BACKGROUND OF THE INVENTION

Cancer remains a leading cause of mortality. In particular, breast cancer has become the most common cancer in women in the United States with 192,570 new cases anticipated in 2009, and it is the second leading cause of cancer death in American women, with 40,470 deaths expected this year (American, Cancer Society. (2009) Cancer Facts & Figures 2009 American Cancer Society). Despite the decades of advances in breast cancer therapies, the mortality rate due to breast cancer has been only slightly reduced in the United States. Over two third of patients initially diagnosed with early stage localized breast cancer eventually develop distant, late-stage disease (Bonadonna, et al. (1995) N Engl J Med 332: 901-906). The 5-year survival rate is still very poor, with about 26% for women with distant metastatic disease and 44% for women with recurrent disease (Giordano, et al. (2004) Cancer 100: 44-52).

Chemotherapy is considered the standard of care for many cancers, including breast cancer. Chemotherapy often decreases tumor size, allowing for subsequent surgery followed by radiation and further adjuvant chemotherapy. However, given that most current anticancer agents do not greatly differentiate between cancerous and normal cells, systemic toxicity and adverse effects (Hassett, et al. (2006) J Natl Cancer Inst 98: 1108-1117) associated with these chemotherapeutics limit their treatment efficacy. In addition, acquired drug resistance further decreases the treatment efficacy of the chemotherapy.

The response rate of breast cancer to first line chemotherapies is encouraging but the majority of patients have tumor progress in 7-10 months. Response to subsequent chemotherapies with various agents drops to 20-30% resulting from formidable cancer chemoresistance (Bernard-Marty, et al. (2004) Oncologist 9, 617-32). A number of mechanisms have been suggested to explain cancer chemoresistance or poor response to chemotherapy. The best studied mechanism of resistance is mediated through the alteration in the drug export pumps responsible for the removal of the therapeutic drugs (Trompier, et al. (2004) Cancer Res 6, 4950-6) Verapamil and its derivative trigger apoptosis through glutathione extrusion by multidrug resistance protein MRP1. One possible way to overcome this drug export pump is to give higher doses of chemotherapy. Although patients treated with high dose chemotherapy had significantly less breast cancer related events, the overall survival rate was not improved because of the treatment toxicity (Farquhar, et al. (2007) Cancer Treatment Reviews 33, 325-337; Farquhar, et al. (2005) Cochrane Database Syst Rev CD003139).

Liposome as a drug delivery carrier has been studied intensively in past several decades, due to its ability to modify the biodistribution of therapeutic agents. Liposomes are closed, self-assembled bilayer membranes, and are non-toxic, non-hemolytic, non-immunogenic, biocompatible/biodegradable, even upon repeated injections (Lian, et al. (2001) J Pharm Sci 90: 667-680; Moghimi, et al. (2001) Pharmacol Rev 53: 283-318). FDA approved liposomes, for example DOXIL which is a formulation of doxorubicin (Northfelt, et al. (1998) J. Clinical Oncology 16, 2445-2451; Ranson, et al. (1997) J Clin Oncol 15, 3185-3191; Gordon, et al. J(2001) Clin Oncol 19, 3312-3322; Al-Batran, et al. (2006) British Journal of Cancer 94, 1615-1620, Chia, et al. (2006) J Clin Oncol. 24, 2773-2778; Jones, et al. (2004) The Lancet Oncology 5, 575-577), can effectively control the pharmacokinetics and biodistribution of the drug, and specific tissues can be avoided or targeted. Thus, therapeutic index enhancement can be achieved both via toxicity reduction and efficacy enhancement (Maeda, et al. (2003) Int Immunopharmacol 3, 319-28.

Drug can be loaded either into the internal, trapped aqueous space, or in the lipid membranes. The grafting of hydrophilic, flexible chains of poly(ethylene glycol) (PEG) on the liposome surface (called "stealth" liposomes) has been shown to prolong their circulation lifetime (10-50 hours versus ~minutes for non-pegylated liposomes alone) (Lasic, et al. (1999) Curr Opin Mol Ther 1: 177-185; Lasic, (1996) Nature 380: 561-562).

With the increase of the circulation time of liposomes, more liposomes are passively accumulated in the tumor tissue by enhanced permeability and retention effect ("EPR effect"), due to the leaky and defective architecture of the tumor vasculature. After accumulation in the tumor tissue, these long circulation liposomes remain in the interstitial space, and eventually release the encapsulated drug in the interstitial space by decomposition, or degradation. Therefore, liposomes are capable of delivery of a high dose of chemotherapy to patients with less systemic exposure. However, liposome releases drug into the interstitial space, and the transportation of the released drug into the tumor cells is a slow process, which allows the drug efflux pumps to effectively remove the drug from the cells, thereby reducing effectiveness.

Targeted liposomes are long circulating liposomes with targeting ligands conjugated to their surface to increase ligand binding efficacy. Immunoliposomes are targeted liposomes wherein the targeting moiety is an antibody, or antibody fragment having antigen-binding ability. Accumulation of the immunoliposomes in tumor tissue is also based on the EPR effect. Different from long circulating liposomes, after accumulation in the tumor tissue, immunoliposomes quickly bind to and internalize in the tumor cell via ligand-receptor interaction, and release the encapsulated drug in the tumor cell. See Mamot et al., Cancer Res 2005; 65:11631-11638. High dose encapsulated drug delivered directly into the tumor cells by the ligand-receptor interaction enhances the ability to overcome cancer drug resistance.

The human epidermal growth factor receptor-2 (Her-2/neu) is found to be overexpressed in ~25%-30% of breast cancer cells. Thus, anti-Her-2/neu immunoliposome has been proposed as a promising delivery system to achieve targeted drug delivery for the treatment of Her-2/neu overexpressing breast cancer. See. e.g., Park et al., Clin Cancer Res. 2002 (4):1172-81.

Targeted delivery of a therapeutic drug to a diseased site can potentially decrease the systemic exposure of chemotherapeutics without sacrificing the therapeutic efficacy.

However, single targeting delivery therapy has its limitation on therapeutic efficacy because there is no targeting moiety that can differentiate all the cancer cells from normal cells. For example only ~25%-30% breast cancer cells overexpress Her-2/neu receptor.

Despite these advances in drug delivery, the heterogeneity of cancer, and breast cancer in particular, restricts the efficacy of treatment. Therefore, there is a critical need to develop more efficacious therapies or delivery methods that decrease systemic toxicity and side effects, and overcome the drug resistance in the cancer patient.

There remains a need for a treatment that can deliver a high dose of chemotherapy to patients with less systemic toxicity.

SUMMARY OF THE INVENTION

Provided is a composition for treating cancer comprising targeted liposomes comprising a chemotherapy agent and a sensitizer for the chemotherapy agent, and non-targeted liposomes comprising an anti-angiogenic agent.

In some embodiments, the targeted liposomes are immunoliposomes. In further embodiments, the immunoliposomes bind to Her-2/neu. In yet further embodiments, the targeted liposomes comprise hydrogenated soy L-α-phosphatidylcholine (HSPC), cholesterol, 1,2-distearoyl-sn-glycero-3-phosphoethanolamine-N-[(polyethylene glycol) 2000] (DSPE-PEG2000) and DSPE-PEG-maleimide. In preferred embodiments, the targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

In some embodiments, the non-targeted liposomes comprise hydrogenated soy L-α-phosphatidylcholine (HSPC), cholesterol, 1,2-distearoyl-sn-glycero-3-phosphoethanolamine-N-[(polyethylene glycol)2000] (DSPE-PEG2000) and DSPE-PEG-maleimide. In preferred embodiments, the non-targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

In some embodiments, the non-targeted liposomes are conjugated to polyethylene glycol. In further embodiments, the chemotherapy agent is doxorubicin, carboplatin, cisplatin, cyclophosphamide, docetaxel, erlotinib, etoposide, fluorouracil, gemcitabine, imatinib mesylate, irinotecan, methotrexate, paclitaxel, sorafinib, sunitinib, topotecan, vincristine or vinblastine. In preferred embodiments, the chemotherapy agent is doxorubicin. In yet further embodiments, the sensitizer is verapamil. In some embodiments, the anti-angiogenic agent is bevacizumab.

In some embodiments, the cancer is breast cancer, cardiac cancer, lung cancer, gastrointestinal cancer, genitourinary tract cancer, liver cancer, bone cancer, nervous system cancer, gynecological cancer, hematologic cancer, skin cancer or adrenal gland cancer.

Provided is a method for treating cancer comprising administering to a subject in need of such treatment targeted liposomes comprising a chemotherapy agent and a sensitizer for the chemotherapy agent, and non-targeted liposomes comprising an anti-angiogenic agent. In further embodiments, the immunoliposomes bind to Her-2/neu. In yet further embodiments, the targeted liposomes comprise hydrogenated soy L-α-phosphatidylcholine (HSPC), cholesterol, 1,2-distearoyl-sn-glycero-3-phosphoethanolamine-N-[(polyethylene glycol)2000] (DSPE-PEG2000) and DSPE-PEG-maleimide. In preferred embodiments, the targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

In some embodiments of the method for treating cancer, the non-targeted liposomes comprise hydrogenated soy L-α-phosphatidylcholine (HSPC), cholesterol, 1,2-distearoyl-sn-glycero-3-phosphoethanolamine-N-[(polyethylene glycol) 2000] (DSPE-PEG2000) and DSPE-PEG-maleimide. In preferred embodiments, the non-targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

In some embodiments of the method for treating cancer, the non-targeted liposomes are conjugated to polyethylene glycol. In further embodiments, the chemotherapy agent is doxorubicin, carboplatin, cisplatin, cyclophosphamide, docetaxel, erlotinib, etoposide, fluorouracil, gemcitabine, imatinib mesylate, irinotecan, methotrexate, paclitaxel, sorafinib, sunitinib, topotecan, vincristine or vinblastine. In preferred embodiments, the chemotherapy agent is doxorubicin. In yet further embodiments, the sensitizer is verapamil. In some embodiments, the anti-angiogenic agent is bevacizumab.

In some embodiments of the method for treating cancer, the targeted liposomes comprising a chemotherapy agent and a sensitizer for the chemotherapy agent are administered to said subject at the same time as said non-targeted liposomes comprising an anti-angiogenic agent. In further embodiments of the method for treating cancer, the targeted liposomes comprising a chemotherapy agent and a sensitizer for the chemotherapy agent are administered to said subject prior to the administration of said non-targeted liposomes comprising an anti-angiogenic agent.

In some embodiments of the method for treating cancer, the cancer is breast cancer, cardiac cancer, lung cancer, gastrointestinal cancer, genitourinary tract cancer, liver cancer, bone cancer, nervous system cancer, gynecological cancer, hematologic cancer, skin cancer or adrenal gland cancer.

Also provided is a kit comprising, in a first compartment, a composition comprising targeted liposomes comprising a chemotherapy agent and a sensitizer for the chemotherapy agent, and, in a second compartment, a composition comprising non-targeted liposomes comprising an anti-angiogenic agent. In some embodiments, the targeted liposomes are immunoliposomes. In further embodiments, the immunoliposomes bind to Her-2/neu. In yet further embodiments, the targeted liposomes comprise hydrogenated soy L-α-phosphatidylcholine (HSPC), cholesterol, 1,2-distearoyl-sn-glycero-3-phosphoethanolamine-N-[(polyethylene glycol)2000] (DSPE-PEG2000) and DSPE-PEG-maleimide. In preferred embodiments, the targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

In some embodiments of the kit, the non-targeted liposomes comprise hydrogenated soy L-α-phosphatidylcholine (HSPC), cholesterol, 1,2-distearoyl-sn-glycero-3-phosphoethanolamine-N-[(polyethylene glycol)2000] (DSPE-PEG2000) and DSPE-PEG-maleimide. In preferred embodiments of the kit, the non-targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

In some embodiments of the kit, the non-targeted liposomes are conjugated to polyethylene glycol. In further embodiments, the chemotherapy agent is doxorubicin, carboplatin, cisplatin, cyclophosphamide, docetaxel, erlotinib, etoposide, fluorouracil, gemcitabine, imatinib mesylate, irinotecan, methotrexate, paclitaxel, sorafinib, sunitinib, topotecan, vincristine or vinblastine. In preferred embodiments, the chemotherapy agent is doxorubicin. In yet further embodiments, the sensitizer is verapamil. In some embodiments, the anti-angiogenic agent is bevacizumab.

DEFINITIONS

As used in the specification and the appended claims, the singular forms "a," "an" and "the" include plural referents unless the context clearly dictates otherwise.

As used herein, the term "antibody" refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies that may be used in the practice of the present invention may exist in a variety of forms including, for example, polyclonal antibodies, monoclonal antibodies, Fv, Fab and F(ab)2, as well as single chain antibodies and humanized antibodies (Harlow et al., 1999, Using Antibodies: A Laboratory Manual, Cold Spring Harbor Laboratory Press, New York; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). The term "antibody" is intended to include antibody fragments that retain antigen-binding activity.

By "anti-angiogenic agent" is meant a substance, when delivered to the extracellular, i.e., interstitial, space of a cancer tissue, inhibits the growth or formation of blood vessels.

By "chemotherapy agent" is meant a substance that is useful for the treatment of a cancer. A chemotherapy agent may be administered with a curative intent or to prolong life or to palliate symptoms. A chemotherapy agent may be administered in conjunction with other cancer treatments, such as radiation therapy or surgery.

As used herein, the terms "treat" and "treatment" are used interchangeably and are meant to indicate a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

As used herein, "individual" or "subject" (as in the subject of the treatment) includes human beings and non-human animals, including both mammals and non-mammals. Mammals include, for example, humans; non-human primates, e.g. apes and monkeys; cattle; horses; sheep; and goats. Non-mammals include, for example, fish and birds.

The expression "effective amount" in connection with the amount of an agent for the treatment of cancer refers to the amount of a composition, or of an active agent, when used in the combinations described herein, induces a state of complete or partial remission of disease, or slows the progression of disease.

The phrase "liposomes" as used herein refers to unilamellar vesicles or multilamellar vesicles such as are described in U.S. Pat. No. 4,753,788, the contents of which are incorporated herein by reference.

The phrase "unilamellar liposomes," as used herein refers to spherical vesicles comprised of one lipid bilayer membrane which defines a single closed aqueous compartment. The bilayer membrane is composed of two layers of lipids; an inner layer and an outer layer (leaflet). The outer layer of the lipid molecules are oriented with their hydrophilic head portions towards the external aqueous environment and their hydrophobic tails pointed downward toward the interior of the liposome. The inner layer of the lipid lays directly beneath the outer layer, the lipids are oriented with their heads facing the aqueous interior of the liposome and their tails towards the tails of the outer layer of lipid.

The phrase "multilamellar liposomes," as used herein refers to liposomes that are composed of more than one lipid bilayer membrane, which membranes define more than one closed aqueous compartment. The membranes are concentrically arranged so that the different membranes are separated by aqueous compartments, much like an onion.

The term "sensitizer" or "chemosensitizer" as used herein is intended to include any agent that renders tumor cells more sensitive to the effects of chemotherapy.

The phrase "targeted liposomes" as used herein refers to liposomes to which a targeting moiety is attached. The targeting moiety binds to a target on cells of the patient. In preferred embodiments, the target is Her2/neu and the liposomes are Her2/neu-targeted liposomes.

The phrase "immunoliposomes" as used herein refers to targeted liposomes wherein the targeting moiety is an antibody or an antibody fragment. Such antibody fragments include, but are not limited to, Fab and F(ab')$_2$ fragments.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

DETAILED DESCRIPTION OF THE INVENTION

An anti-angiogenic agent, as an extracellular drug, is selectively delivered to the interstitial space of cancer tissue;

and a chemotherapy agent and a sensitizer for the chemotherapy agent, as intracellular therapeutic agents, are selectively delivered to the inside of the cancer cells by internalization utilizing an appropriate ligand-receptor interaction to circumvent undesirable side effects and overcome drug resistance. The anti-angiogenic agent is contained in a non-targeted liposome. The chemotherapy agent and its sensitizer are contained in a targeted liposome. In the immunoliposomes, incorporated targeting moieties highly specific to the surface of cancer cells facilitate the internalization of the therapeutic drug and its sensitizer into the tumor cells to overcome drug resistance. The non-targeted liposome selectively delivers an extracellular therapeutic drug, i.e., an anti-angiogenic agent, to the interstitial space to inhibit the tumor growth by interfering with cell-cell communications. The combination therapy maintains efficacious systemic drug levels with a sustained release profile. The combination therapy is designed to not only decrease systemic toxicity and side effects, but also to reduce drug resistance. The administration of three different classes of chemotherapeutic agents, carried in targeted and non-targeted liposome compositions, thus provides an improved platform for cancer treatment, including but not limited to, breast cancer.

The liposomes utilized herein may be either unilamellar or multilamellar in nature, the latter defining more than one closed aqueous compartment.

Liposomes suitable for use in the compositions of the present invention include those composed primarily of vesicle-forming lipids. Such a vesicle-forming lipid is one which can form spontaneously into bilayer vesicles in water. The lipid bilayer preferably contains at least a phospholipid as its main component.

The vesicle-forming lipids are preferably lipids having two hydrocarbon chains, typically acyl chains, and a head group, either polar or nonpolar. Synthetic vesicle-forming lipids and naturally-occurring vesicle-forming lipids include, for example, phospholipids, where the two hydrocarbon chains are typically between about 14-22 carbon atoms in length, and have varying degrees of unsaturation. The above-described lipids and phospholipids whose carbon chains have varying degrees of saturation can be obtained commercially or prepared according to published methods. Other suitable lipids include glycolipids, cerebrosides and sterols, such as cholesterol.

Exemplary phospholipids include glycerophospholipids such as phosphatidylcholine (lecithin), phosphatidylglycerol, phosphatidic acid, phosphatidylethanolamine, phosphatidylserine, and phosphatidylinocitol; sphingophospholipids such as sphingomyelin; natural or synthetic diphosphatidyl phospholipids such as cardiolipin, and derivatives thereof. The phospholipid may be hydrogenated by a method commonly used in the art (for example, hydrogenated soybean phosphatidyl choline). Preferred phospholipids are hydrogenated phospholipids such as hydrogenated soybean phosphatidyl choline (HSPC), e.g., hydrogenated soy L-α-phosphatidylcholine. The liposome may contain either single phospholipid or a plurality of phospholipids as its main membrane component.

The liposome may also contain a membrane component other than the main lipid component described above. For example, the liposome may be formed from a mixture of a phospholipid and a lipid other the phospholipid or a derivative of such lipid, capable of stable incorporation into lipid bilayers, to form the membrane of the liposome. Examples of such additional lipids include glyceroglycolipids, sphingoglycolipids, and sterols such as cholesterol.

The exterior of the lipid bilayer may be modified with a hydrophilic macromolecule. Examples include polyethylene glycol, polyglycerin, polypropylene glycol, polyvinyl alcohol, styrene-maleic anhydride alternating copolymer, divinyl ether-maleic anhydride alternating copolymer, polyvinylpyrrolidone, polyvinylmethylether, polyvinylmethyloxazoline, polyethyloxazoline, polyhydroxy-propyloxazoline, polyhydroxypropylmethacrylamide, polyumethacrylamide, polydimethylacrylamide, polyhydroxypropyl methacrylate, polyhydroxyethyl acrylate, hydroxymethylcellulose, hydroxyethylcellulose, polyaspartamide, and synthetic polyamino acid. The hydrophilic macromolecule can increase prolong the stability of the liposome in vivo. Preferred hydrophilic macromolecules are polyethylene glycol (PEG), polyglycerin (PG), and polypropylene glycol (PPG). The PEG may typically have a molecular weight of 500 to 10,000 Daltons, preferably 1,000 to 7,000 Daltons, and more preferably 2,000 to 4,000 Daltons.

The hydrophilic macromolecule moiety may be introduced into the liposome membrane by a lipid derivative of the hydrophilic macromolecule. In certain embodiments, the lipid portion of the lipid derivative of the hydrophilic macromolecule may comprise, for example, a phospholipid. The acyl chain included in the phospholipid may comprise, for example, a saturated fatty acid, for example a $C_{14}$-$C_{20}$ fatty acid. Exemplary of such acyl chains include dipalmitoyl, distearoyl, and palmitoyl stearoyl.

The phospholipid portion of the lipid derivative of the hydrophilic macromolecule may include a functional group which can react with the hydrophilic macromolecule to form the lipid derivative of the hydrophilic macromolecule. Examples of a phospholipid having a functional group reactive with the hydrophilic macromolecule include phospholipids comprising amino, hydroxyl and carboxy groups, such as phosphatidyl ethanolamine (amino group), phosphatidylglycerol (hydroxy group), and phosphatidylserine (carboxy group).

Particular lipid derivatives of the hydrophilic macromolecules may be formed by the bonding of a phospholipid; an additional lipid such as sterol; an aliphatic alcohol; an aliphatic amine; a glycerin fatty acid ester; and PEG, PG, or PPG, with PEG being preferred. One such preferred one PEG-derivatized phospholipid is 1,2-distearoyl-sn-glycero-3-phosphoethanolamine-N-[(polyethylene glycol) (DSPE-PEG). In one embodiment, the PEG has a molecular weight of about 2,000 Daltaons (DSPE-PEG-2000). In preferred embodiments, the liposome comprises at least one PEG-derivatized phospholipid. Incorporation of PEG-derivatized lipids in liposomal membranes results in formation of sterically stabilized liposomes ("stealth liposomes"), possessing an extended long circulation time. See e.g., Lasic et al., *Curr Opin Mol Ther* 1:177-185 (1999); Lasic, *Nature* 380: 561-562 (1996).

Preparation of vesicle-forming lipids derivatized with hydrophilic polymers has been described, for example in U.S. Pat. No. 5,395,619. Preparation of liposomes including such derivatized lipids has also been described, where typically between 1-20 mole percent of such a derivatized lipid is included in the liposome formulation (see, for example, U.S. Pat. No. 5,013,556).

The liposomes may be formed according to well-known methods, which are summarized, for example, in U.S. Pat. No. 8,241,663.

Drug loading of liposomes may be accomplished, for example, by a method in which the lipid layer constituting the liposome is hydrated with an aqueous solution containing the drug to thereby load the drug in the liposome (passive loading), or by a method in which an ion gradient is formed between the interior and the exterior of the liposome layer so that the drug permeates through the liposome layer according to the ion gradient to become loaded in the liposome (remote loading). See e.g., U.S. Pat. No. 5,192,549, and U.S. Pat. No. 5,316,771.

The aforementioned materials and methods may be utilized for preparing non-targeted liposomes incorporating one or more anti-angiogenic agents. For preparation of targeted liposomes comprising one or more chemotherapy agents and one or more sensitizers for the chemotherapy agent(s), the same materials and procedures may be utilized, provided that the liposome exterior surface is suitably formed or derivatized to contain a functional group comprising, or for attaching to, a targeting moiety. Where the targeted liposome is an immunoliposome, the liposome-forming materials in one embodiment may include a component comprising a functional group capable of linking to a functional group of an antibody or antibody fragment, or to an appropriately modified functional group of an antibody or antibody fragment. Such antibody fragments include, but are not limited to, Fab and F(ab')$_2$ fragments.

The targeting moiety on the target liposome, e.g. an antibody or antibody fragment, is selected to bind a target ligand that is preferably found on the surface of a tissue or cell. Preferably, the target ligand is on which is preferentially expressed or overexpressed by cancer cells/tissues targeted for treatment. In one embodiment, the cancer treated is breast cancer and the target ligand is HER2 (c-erbB-2, new), a proto-oncogene encoded growth factor receptor. Other target ligands include, for example, other growth factor receptors associated with cancers such as EGFR (HER1), HER3 and HER4. Other targets associated with particular cancers are known in the art.

In some embodiments, the antibody or antibody fragment is covalently attached to the free distal end of a hydrophilic polymer chain, e.g., PEG, which is attached to or embedded in a vesicle-forming lipid. There are a wide variety of techniques for attaching a selected hydrophilic polymer to a selected lipid and activating the free, unattached end of the polymer for reaction with a selected ligand, in particular, PEG. See, e.g., Allen, et al., *Biochemicia et Biophysica Acta*, 1237:99-108 (1995); Zalipsky, *Bioconjugate Chem.*, 4(4): 296-299 (1993); Zalipsky, et al. FEBS Lett., 353:71-74 (1994); Zalipsky, et al., *Bioconjugate Chemistry*, 6(6):705-708 (1995); Zalipsky, in *STEALTH LIPOSOMES* (D. Lasic and F. Martin, Eds.) Chapter 9, CRC Press, Boca Raton, Fla. (1995)).

Generally, the hydrophilic polymer, e.g., PEG, chains may be functionalized to contain reactive groups suitable for coupling with, for example, sulfhydryls, amino groups, and aldehydes or ketones (typically derived from mild oxidation of carbohydrate portions of an antibody) present in a wide variety of ligands. Thus, in some embodiments, an antibody or antibody fragment is attached to the distal end of PEG chains on the liposome surface to form immunoliposomes via a linker. Examples of such PEG-terminal reactive groups include maleimide (for reaction with sulfhydryl groups), N-hydroxysuccinimide (NHS) or NHS-carbonate ester (for reaction with primary amines), hydrazide or hydrazine (for reaction with aldehydes or ketones), iodoacetyl (preferentially reactive with sulfhydryl groups) and dithiopyridine (thiol-reactive). Synthetic reaction schemes for activating PEG with such groups are set forth in U.S. Pat. Nos. 5,631,018, 5,527,528, 5,395,619, and the relevant sections describing synthetic reaction procedures are expressly incorporated herein by reference.

In certain embodiments, the immunoliposome comprises a PEG-terminal reactive maleimide, for coupling with a thiolated antibody/antibody fragment which will serve as the targeting moiety on the immunoliposome. Maleimide functionalization may be achieved by including in the vesicle-forming lipids an appropriately maleimide-functionalized lipid, such as 1,2-distearoyl-sn-glycero-3-phosphoethanolamine-N-[(polyethylene glycol)-maleimide, e.g., DSPE-PEG2000 maleimide.

Targeted liposomes, such as immunoliposome, may be prepared by allowing drug-loaded (i.e., loaded with chemotherapy agent and sensitizer) vesicles to react with the appropriate targeting ligand under appropriate conditions. To prepare immunoliposomes, the antibody used as the targeting ligand may be first modified to generate appropriate reactive groups on the antibody for covalent binding to liposome components. For example, the antibody is modified with succinimidyl acetylthioacetate (SATA) or 2-iminothiolane (Traut's reagent) at pH 8.0 to introduce thiol groups (Derksen and Scherphof, *Biochimica et Biophysica Acta* 814: 151-155, 1985). The thiolated antibody is then coupled with maleimide groups, such as a DSPE-PEG2000 component of the liposomes, at pH 6.5. In certain embodiments, the molar ratio of Ab-SH to maleimide is 1:40 using an Ab-SH concentration of 0.3 mg/ml. The reaction is carried out >12 hours at 4° C., is stopped and unconjugated antibody is separated from the liposomes by, e.g., ultracentrifugation for 1 hour at 30,000 rpm. Alternatively, the antibody-containing liposomes can be separated from free antibody by column chromatography using, e.g., a Sephadex CL-4B column pre-equilibrated with saline. Previous studies (Nallamothu et al., *AAPS Pharm Sci Tech* 7: E32, 2006; Pattillo et al., *Pharm Res* 22: 1117-1120, 2005.) have shown that this results in a sufficient number of antibodies being attached to each liposomal particle to cause an attachment of the particle to the antigen. While a 1:40 ratio of Ab-SH to maleimide group is an acceptable ratio for antibody attachment, other ratios, such as ratios in the range of 1:10 to 1:100 may be utilized to optimize drug delivery. While antibody attachment to drug-loaded liposomes is exemplified by resort to drug-loaded liposomes comprising DSPE-PEG2000 as the membrane component for antibody attachment, other membrane components may be substituted for DSPE-PEG2000 in providing functional groups for covalent attachment of antibodies and antibody fragments.

In one embodiment, an exemplary long-circulation liposome, which may be used as the non-targeted liposome or may be decorated with antibody to form a targeted antibody, is composed of hydrogenated soy L-α-phosphatidylcholine (HPSC), cholesterol, 1,2-distearoyl-sn-glycero-3-phosphoethanolamine-N-[(polyethylene glycol)2000] (DSPE-PEG2000) and DSPE-PEG2000 maleimide. In one embodiment, the liposome is composed of about 50 mole % hydrogenated soy L-α-phosphatidylcholine (HSPC), about 45 mole % cholesterol, about 3 mole % DSPE-PEG2000 and about 2 mole % DSPE-PEG2000-maleimide. To form the liposomes, the lipids are mixed. Then the lipids are dried under vacuum overnight. The resulting lipid film is rehydrated in 40° C. deionized water to form vesicles. The lipids are then extruded using, e.g., a Lipex™ extruder (Vancouver, BC, Canada) ten times with a 0.2 micron filter (Nucleopore) yielding a liposome diameter of 196 ±3 nm (Scott et al., *FASEB J.* 23(10): 3361-3367, 2009).

The targeted liposomes comprise a chemotherapy agent and a sensitizer for the chemotherapy agent. The chemotherapy agent may be any chemotherapy agent that may be used to treat the cancer that is being treated by the method of the present invention.

Anti-cancer therapeutic agents that can be utilized in the targeted liposomes include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukins; interferons; iproplatin; irinotecan hydrochloride; lanreotide acetate; letrozole; leuprolide; leuprolide; acetate; liarozole hydrochloride; lometrexol sodium; lomustine; losoxantrone; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs include, but are not limited to: 5-ethynyluracil; abiraterone; acylfulvene; adecypenol; ALL-TK antagonists; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogens; antiestrogens; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bisaziridinylspermine; bisnafide; bistratene A; breflate; budotitane; buthionine sulfoximine; calcipotriol; calphostin C; camptothecin derivatives; canarypox IL-2; capecitabine; carboxamide-amino-triazole; carboxyamidotriazole; casein kinase inhibitors (ICOS); castanospermine; cecropin B; cetrorelix; chlorins; chloroquinoxaline sulfonamide; cicaprost; cis-porphyrin; clomifene analogues; clotrimazole; collismycin A; collismycin B; combretastatin A4; combretastatin analogues; conagenin; crambescidin 816; crisnatol; cryptophycin 8; cryptophycin A derivatives; curacin A; cyclopentanthraquinones; cyclophosphamide; cycloplatam; cypemycin; cytarabine ocfosfate; cytolytic factor; cytostatin; dacliximab; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-dioxamycin; diphenyl spiromustine; docetaxel; docosanol; dolasetron; doxifluridine; doxorubicin; dronabinol; duocarmycin SA; ebselen; ecomustine; edelfosine; edrecolomab; eflornithine; elemene; emitefur; epirubicin; episteride; erlotinib; estrogen agonists; estrogen antagonists; exemestane; fadrozole; fazarabine; filgrastim; finasteride; flavopiridol; flezelastine; fluasterone; fludarabine; fluorodaunorunicin hydrochloride; 5-fluorouracil; forfenimex; formestane; fostriecin; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idarubicin; idoxifene; idramantone; ilomastat; imatinib mesylate; imidazoacridones; imiquimod; immunostimulant peptides; insulin-like growth factor-1 receptor inhibitor; interferon agonists; interferons; interleukins; iobenguane; iododoxorubicin; ipomeanol, irinotecan; 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; leucovorin; leukemia inhibiting factor; leukocyte alpha interferon; leuprorelin; levamisole; liarozole; lipophilic disaccharide peptide; lipophilic platinum compounds; lissoclinamide 7; lobaplatin; lombricine; lometrexol; lonidamine; lovastatin; loxoribine; lurtotecan; lutetium texaphyrin; lysofylline; lytic peptides; maitansine; mannostatin A; marimastat; maspin; matrilysin inhibitors; matrix metalloproteinase inhibitors; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitoxantrone; mofarotene; molgramostim; mopidamol; multiple drug resistance gene inhibitor; mustard anticancer agent; mycaperoxide B; myriaporone; N-acetyldinaline; N-substituted benzamides; nafarelin; nagrestip; napavin; naphterpin; nartograstim; nedaplatin; nemorubicin; neridronic acid; neutral endopeptidase; nilutamide; nisamycin; nitric oxide modulators; nitroxide antioxidant; nitrullyn; $O^6$-benzylguanine; octreotide; okicenone; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; prednisone; propyl bis-acridone; prostaglandin J2; proteasome inhibitors; protein A-based immune modulator; protein tyrosine phosphatase inhibitors; purine nucleoside phosphorylase inhibitors; purpurins; pyrazoloacridine; raf antagonists; raltitrexed; ramosetron; ras farnesyl protein transferase inhibitors; ras inhibitors; ras-GAP inhibitor; retelliptine demethylated; rhizoxin; rohitukine; romurtide; roquinimex; rubiginone B1; ruboxyl; safingol; saintopin; SarCNU; sarcophytol A; sargramostim; semustine; senescence derived inhibitor 1; sizofuran; sobuzoxane; sodium borocaptate; sodium phenylacetate; sorafenib; solverol; sonermin; sparfosic acid; spicamycin D; spiromustine; splenopentin; spongistatin 1; squalamine; stipiamide; sulfinosine; sunitinib; superactive vasoactive intestinal peptide antagonist; suradista; suramin; swainsonine; tallimustine; tamoxifen; tamoxifen methiodide; tauromustine; tazarotene; tecogalan sodium; tegafur; tellurapyrrylium; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Preferred chemotherapeutic agents include: carboplatin, cisplatin, cyclophosphamide, docetaxel, erlotinib, etoposide, 5-fluorouracil, gemcitabine, imatinib mesylate, irinotecan, methotrexate, paclitaxel, sorafinib, sunitinib, topotecan, vincristine and vinblastine. In certain embodiments, the chemotherapeutic agent is anthracycline-based anticancer agent. Such agents include, for example, doxorubicin, daunorubicin, epirubicin, idarubicin, valrubicin, mitoxantrone, or a combination thereof. Doxorubicin is particularly preferred.

The sensitizer for the chemotherapy agent may be any sensitizer that is capable of increasing the effectiveness of the chemotherapy agent. In one embodiment, the chemosensitizer may be a protein inhibitor that counteracts drug resistance, such as, multidrug resistance protein-1 (MDR1) inhibitors, MDR-2 inhibitors, multidrug resistance related protein-1 (MRP-1) inhibitors, and breast cancer resistance protein (BCRP) inhibitors. Other sensitizers include, for example, cyclosporin A, verapamil, bricodar and reversan, and combinations thereof. In preferred embodiments, the sensitizer for the chemotherapy agent is verapamil, i.e., (RS)-2-(3,4-dimethoxyphenyl)-5-{[2-(3,4-dimethoxyphenyl]-(methyl)amino}-2-prop-2-ylpentanenitrile)), or a derivatives thereof. Verapamil is a resistance modifier that modifies the fluidity of the cell membrane and increases the effectiveness of doxorubicin.

In preferred embodiments, a combination of a chemotherapeutic agent, such as doxorubicin, and its sensitizer, such as verapamil, is selectively delivered to cancer cells, such as breast tumor cells, by targeted liposomes to overcome chemoresistance.

The non-targeted liposomes of the invention comprise an anti-angiogenic agent. The anti-angiogenic agent for loading into the non-targeted liposome may comprise an agent that blocks the angiogenic activity of an angiogenic factor or its receptor. The anti-angiogenic agent can be naturally occurring or non-naturally occurring. For example, an anti-angiogenic agent may comprise an antibody or other antagonist to an angiogenic agent, e.g., antibodies to VEGF-A or to the VEGF-A receptor; anti-PDGFR inhibitors (e.g., Gleevec™ (imatinib mesylate)); small molecules that block VEGF receptor signaling (e.g., PTK787/ZK2284, SU6668, SUTENT™/SU11248 (sunitinib malate); AMG706; and those anti-angiogenic agents described in, e.g., international patent application WO 2004/113304). Anti-angiogenic agents may further include, but are not limited to, the following agents: VEGF inhibitors such as a VEGF-specific antagonist, EGF inhibitor, EGFR inhibitors, Erbitux™ (cetuximab, ImClone Systems, Inc., Branchburg, N.J.), Vectibix™ (panitumumab, Amgen, Thousand Oaks, Calif.), TIE2 inhibitors, IGF 1R inhibitors, COX-II (cyclooxygenase II) inhibitors, MMP-2 (matrix-metalloproteinase 2) inhibitors, and MMP-9 (matrix-metalloproteinase 9) inhibitors, CP-547,632 (Pfizer Inc., N.Y., USA), Axitinib (Pfizer Inc.; AG-013736), ZD-6474 (AstraZeneca), AEE788 (Novartis), AZD-2171), VEGF Trap (Regeneron/Aventis), Vatalanib (also known as PTK-787, ZK-222584: Novartis & Schering A G), Macugen (pegaptanib octasodium, NX-1838, EYE-001, Pfizer Inc./Gilead/Eyetech), IM862 (Cytran Inc. of Kirkland, Wash., USA); and angiozyme, a synthetic ribozyme from Ribozyme (Boulder, Colo.) and Chiron (Emeryville, Calif.); and combinations thereof. Other angiogenesis inhibitors include thrombospondin 1, thrombospondin 2, collagen IV and collagen XVIII. VEGF inhibitors are disclosed in U.S. Pat. Nos. 6,534,524 and 6,235,764. Anti-angiogenic agents also include native angiogenesis inhibitors, e.g., angiostatin and endostatin. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12):1359-1364; Tonini et al. (2003) *Oncogene* 22:6549-6556 (e.g., Table 2 listing known anti-angiogenic factors); and, Sato (2003) *Int. J Clin. Oncol.* 8:200-206 (e.g., Table 1 listing anti-angiogenic agents used in clinical trials).

In preferred embodiments, the anti-angiogenic agent is bevacizumab, also known as "rhuMAb VEGF" or "AVASTIN™," (rhuMAbVEGF, Avastin; Genentech), a recombinant humanized anti-VEGF monoclonal antibody which inhibits angiogenesis by specifically binding to VEGF and preventing it from binding to the receptor.

The anti-angiogenic agent is selectively delivered to the interstitial space of breast cancer tissue by non-targeted liposomes to inhibit tumor growth.

In the various liposome embodiments discussed above, the contained pharmaceutical agent, i.e., chemotherapeutic agent, sensitizer or anti-angiogenic agent, may be contained in the interior space of the liposome, within the lipid bilayer of the liposomes, or both.

The targeted and non-targeted liposomes may be contained in a pharmaceutical composition comprising the liposome(s) and a pharmaceutically acceptable carrier or a diluent Such carriers and diluents are well known in the art. The carrier or diluent may be, for example, water (saline or sterile water), Ringer's solution, phosphate buffered saline, dextrose solution, maltodextrose solution, glycerol or ethanol.

Compositions comprising the targeted and/or non-targeted liposomes may be administered by any suitable route, such as parenteral administration. The parenteral administration, for example, may be intravenous, intra-arterial, intradermal, intramuscular, intracavity (abdominal cavity, joints, or eye), rectal, intraperitoneal, subcutaneous, topical or by direct injection. The direct injection may involve injecting directly into a diseased site such as a tumor site. The liposome may be administered intravenously and thereby brought to the target site such as a tumor site by blood flow.

In one embodiment, the combination of targeted and non-targeted liposomes are co-formulated and used as part of a single pharmaceutical composition or dosage form. The composition may be administered by any route and according to any schedule which is sufficient to bring about the desired therapeutic effect in the patient.

Alternatively, according to other embodiments, the targeted and non-targeted liposomes may be formulated and administered as two or more separate compositions. The separate compositions may be administered by the same or different routes, administered at the same time or different times, and administered according to the same schedule or on different schedules, provided the dosing regimen is sufficient to bring about the desired therapeutic effect in the patient. When the targeted and non-targeted liposome compositions are administered in serial fashion, it may prove practical to intercalate administration of the two compositions, wherein a time interval, for example a 0.1 to 48 hour period, separates administration of the compositions.

The amount of liposome formulation administered to obtain the therapeutic benefit will, of course, be determined by the nature of the contained drug(s), the degree of drug loading of the liposome, and the particular circumstances of the individual patient. Such circumstances include the size, weight, age and sex of the patient, the nature and stage of the disease, the aggressiveness of the disease, and the route of administration. For the chemotherapeutic agent and anti-angiogenic agents, a starting point for the determination of a suitable dose is the dose at which the agent has been found to be safe and effective either alone or in combination with other chemotherapeutic agents. For marketed drugs, suitable doses and dosing protocols are recommended by the manufacturer and published, for example in the *Physician's Desk Reference*, 58$^{th}$ Edition (Thomson Healthcare, 2004), or 60$^{th}$ Edition (Thomson Healthcare, 2006), the entire disclosures of which are incorporated herein by reference.

The compositions are believed to be useful in treating a broad range of tumor types, including but not limited to the following: ovarian cancer, cervical cancer, breast cancer, prostate cancer, testicular cancer, lung cancer, renal cancer, colorectal cancer, skin cancer, brain cancer, and tumors that may arise from hematological malignancies such as leukemias, including acute myeloid leukemia, chronic myeloid leukemia, acute lymphoid leukemia and chronic lymphoid leukemia.

More particularly, cancers that may be treated by the compounds, compositions and methods of the invention include, but are not limited to, the following:

cardiac cancers, including, for example sarcoma, e.g., angiosarcoma, fibrosarcoma, rhabdomyosarcoma, and liposarcoma, myxoma, rhabdomyoma, fibroma, lipoma and teratoma;

lung cancers, including, for example, bronchogenic carcinoma, e.g., squamous cell, undifferentiated small cell, undifferentiated large cell, and adenocarcinoma, alveolar and bronchiolar carcinoma, bronchial adenoma, sarcoma, lymphoma, chondromatous hamartoma, and mesothelioma;

gastrointestinal cancer, including, for example, cancers of the esophagus, e.g., squamous cell carcinoma, adenocarcinoma, leiomyosarcoma, and lymphoma, cancers of the stomach, e.g., carcinoma, lymphoma, and leiomyosarcoma, cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma, cancers of the large bowel, e.g., adenocarcinoma, tubular adenoma, villous adenoma, hamartoma, and leiomyoma, genitourinary tract cancers, including for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma, cancers of the prostate, e.g., adenocarcinoma and sarcoma, cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g. hepatocellular carcinoma, cholangiocarcinoma, hepatoblastoma, angiosarcoma, hepatocellular adenoma, and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g. osteoma, hemangioma, granuloma, xanthoma, and osteitis deformans, cancers of the meninges, e.g. meningioma, meningiosarcoma, and gliomatosis, cancers of the brain, e.g. astrocytoma, medulloblastoma, glioma, ependymoma, germinoma (pinealoma), glioblastoma multiform, oligodendroglioma, schwannoma, retinoblastoma, and congenital tumors, and cancers of the spinal cord, e.g. neurofibroma, meningioma, glioma and sarcoma;

gynecological cancers, including, for example, cancers of the uterus, e.g., endometrial carcinoma, cancers of the cervix, e.g., cervical carcinoma, and pre-tumor cervical dysplasia, cancers of the ovaries, e.g. ovarian carcinoma, including serous cystadenocarcinoma, mucinous cystadenocarcinoma, unclassified carcinoma, intraepithelial carcinoma, adenocarcinoma, fibrosarcoma, and melanoma, cancers of the vagina, e.g. clear cell carcinoma, squamous cell carcinoma, botryoid sarcoma, and embryonal rhabdomyosarcoma, and cancers of the fallopian tubes, e.g. carcinoma;

hematologic cancers, where they result in the formation of tumor tissues, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis, and adrenal gland cancers, including, for example, neuroblastoma.

Cancers may comprise solid tumors that may or may not be metastatic. Cancers may also occur, as in leukemia, as a diffuse tissue. Thus, the term "tumor cell," as provided herein, includes a cell afflicted by any one of the above identified disorders.

The liposome compositions may be provided in a pharmaceutical pack or kit comprising one or more containers or compartments filled with one or more compositions. Optionally associated with such container(s) is a notice in the form prescribed by a governmental agency regulating the manufacture, use or sale of pharmaceuticals or biological products, which notice reflects approval by the agency of manufacture, use or sale for human administration. Also optionally included with such container(s) are instructions for carrying out the methods of the invention.

In one embodiment, a kit comprises, in a first compartment, a composition comprising targeted liposomes comprising a chemotherapy agent and a sensitizer for the chemotherapy agent, and, in a second compartment, a composition comprising non-targeted liposomes comprising an anti-angiogenic agent.

The instructional material may comprise a publication, a recording, a diagram, or any other medium of expression which can be used to communicate the usefulness of the method. The package insert may comprise text housed in any physical medium, e.g., paper, cardboard, film, or may be housed in an electronic medium such as a diskette, chip, memory stick or other electronic storage form. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

The practice of the invention is illustrated by the following non-limiting examples.

EXAMPLES

Example 1

Preparation of Liposomes and of Immunoliposomes Conjugated to anti-Her-2/neu Antibody; Determination of Binding to Her-2/neu antigen.

A. Liposome Preparation

Liposomes composed of 50 mol % hydrogenated soy L-α-phosphatidylcholine (HSPC), 45 mol % cholesterol, 3 mol % 1,2-distearoyl-sn-glycero-3-phosphoethanolamine-N-[(polyethylene glycol)2000] (DSPE-PEG2000) and 2 mol % DSPE-PEG2000-maleimide (Avanti, Alabaster, Ala.) were prepared as follows. After mixing, the lipids were dried under vacuum overnight, and then the lipid film was rehydrated in 40° C. deionized water to form vesicles. The lipids were extruded (Lipex, Vancouver, BC, Canada) 10 times with a 0.2 micron filter (Nucleopore) yielding liposomes with a diameter of 196±3 nm.

B. Immunoliposome Preparation

Immunoliposomes wherein the targeting ligand is anti-Her-2/neu antibody were also prepared. A mouse monoclonal antibody against Her-2/neu (Thermo Scientific, Fremont, Calif.) was covalently linked to DSPE-PEG(2000)-maleimide in the HSPC and cholesterol-based liposomes prepared in A., above, as follows.

The antibody was first modified with succinimidyl acetylthioacetate (SATA) or 2-iminothiolane (Traut's reagent) at pH 8.0 to introduce thiol groups. The thiolated antibody was then coupled with maleimide groups on the DSPE-PEG2000 component of the liposomes at pH 6.5. The molar ratio of Ab-SH to maleimide was 1:40 using an Ab-SH concentration of 0.3 mg/ml. The reaction carried out for more than 12 hours at 4° C. was stopped. Unconjugated antibody was separated from the liposomes by ultracentrifugation for 1 hour at 30,000 rpm. After linking the antibody, the liposome size grew from 196.8±2.7 nm to 202.8±3.8 nm, as determined by dynamic light scattering.

The binding abilities of both liposomes and immunoliposomes to Her-2/neu were evaluated in an in vitro setting. Briefly, both liposomes and immunoliposomes were labeled with a fluorescent dye (Carboxyfluorescein) (Avanti, Alabaster, Ala.). A 96 well plate was coated with Her-2/neu antigen (Thermo Scientific, Fremont Calif.). Either immunoliposomes or liposomes were incubated on the plate. After several washes, the fluorescent intensity was measured using an IVIS 50 optical imaging system (Xenogen Corp.)

Figure 1:
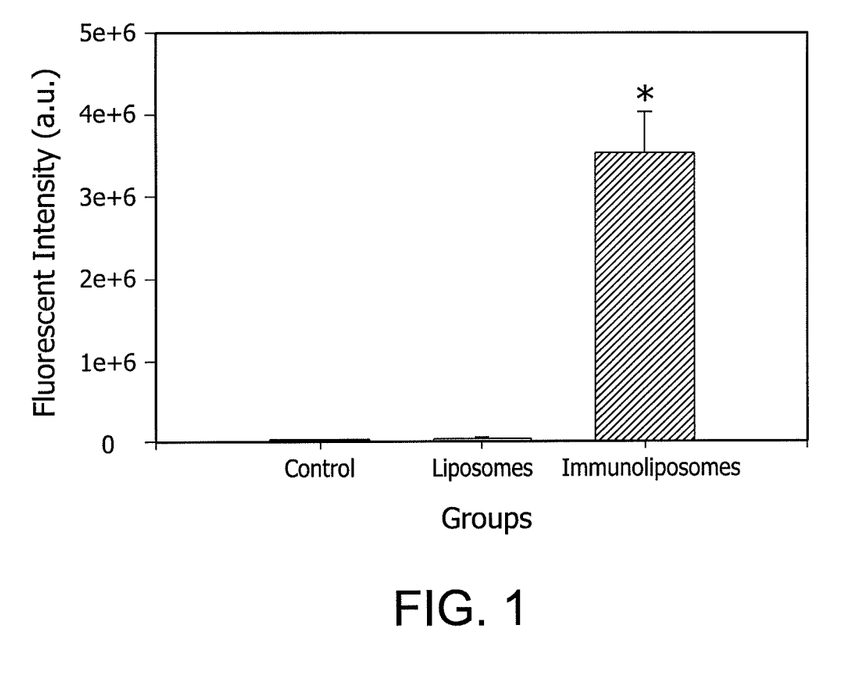
FIG. 1 compares the binding abilities of liposomes and immunoliposomes conjugated to anti-Her-2/neu antibody on antigen-coated and non-coated well plates. The groups are labeled as follows. Control: immunoliposomes on non-coated wells. Liposomes: liposomes on coated wells. Immunoliposomes: immunoliposomes on coated wells. (n=4, *P<0.05).

In Her-2/neu antigen coated wells, immunoliposomes showed a significant increase (100-fold) in fluorescent intensity compared with liposomes (FIG. 1). While a large number of the immunoliposomes attached to the Her-2/neu coated wells, there was almost no adhesion to non-coated wells (FIG. 1, "Control"). These results demonstrate that immunoliposomes conjugated to anti-Her-2/neu antibody can bind to their target Her-2/neu antigen. These results also indicate that immunoliposomes can be selectively targeted to Her-2/neu overexpressing cancer cells.

Example 2

Determination of Antibody Coupling Efficiency and Antibody Density on Immunoliposome Surface Analysis of elution profiles allows determination of antibody coupling efficiency. Lipid concentration and the coupling efficiency of mAb to liposomes is estimated by the phosphorous assay (Fiske, et al. (1925) *J Biol Chem* 66: 375-400) and the BCA protein assay kit (Pierce), respectively. Coupling efficiency is calculated from the ratio of protein:phospholipid. The average number of mAb per liposome is calculated by using the above values. The conversion of mg of mAb per mmol of phospholipids to the number of mAb molecules conjugated per liposome is based on the assumption that a 200-nm liposome contains ~200,000 molecules of conventional phospholipids (Hansen, et al. (1995) *Biochim Biophys Acta* 1239: 133-144) and half of that amount for HSPC lipids.

Example 3

Preparation of Drug-Loaded Liposomes/Immunoliposomes; Drug Release Profiles

Drugs (bevacizumab for liposomes, and doxorubicin and verapamil for immunoliposomes) were encapsulated into liposomes by a dehydration-rehydration method described by Scott, et al. (2009) *FASEB J*, 23(10), 3361-336728. Briefly, the liposomes were freeze dried under vacuum overnight. The liposomes were rehydrated in 1 mL of a Tris buffer (pH 7.4) solution containing drugs at 40° C. and vortexed until vesicles were fully reformed and then incubated at room temperature for 1 hour. Un-entrapped drug was separated from liposomes by passing a diluted sample through Sephadex G-50 column.

Figure 2A:
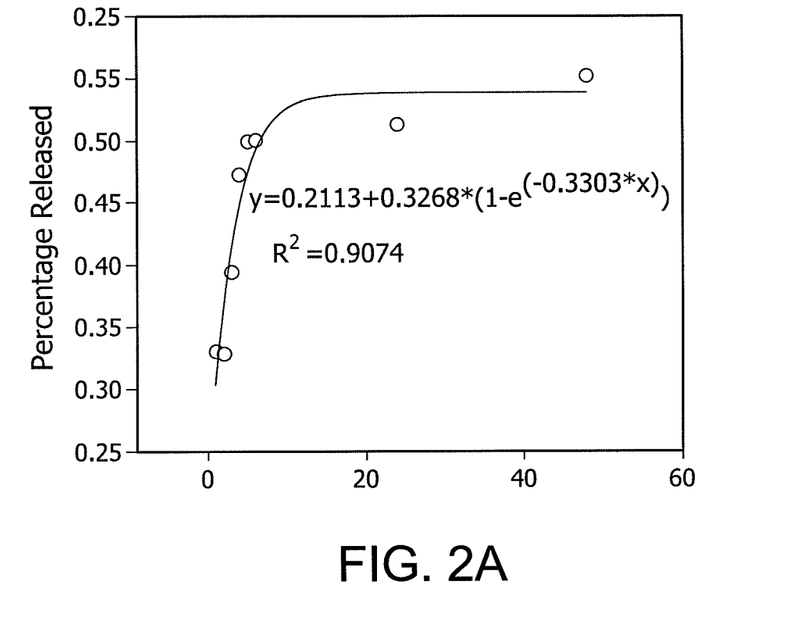
FIG. 2A shows the release profile of bevacizumab from liposome over time (hours)
Figure 2B:
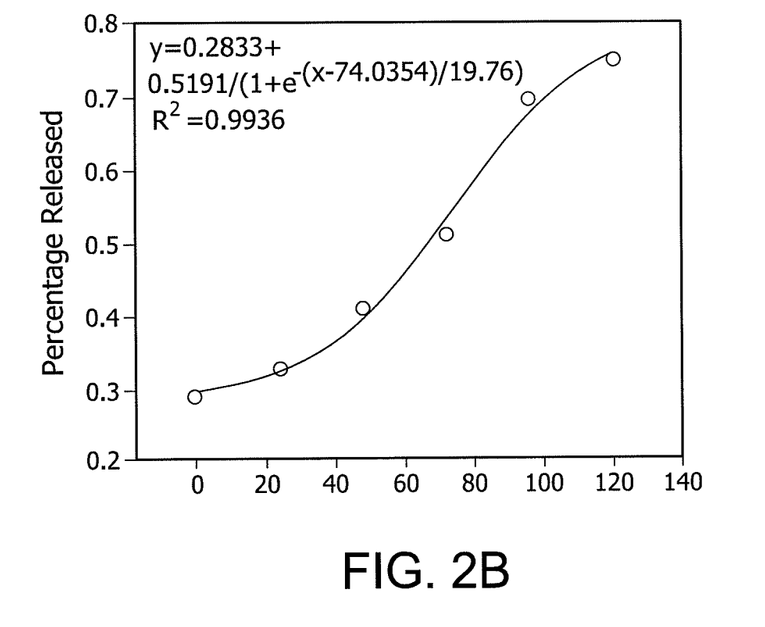
FIG. 2B shows the release profile of doxorubicin from immunoliposomes over time (hours).

The release profile of bevacizumab from liposomes was obtained by direct enzyme-linked immunosorbent assay (ELISA). The results are shown in FIG. 2A (x axis=time in hours). The release profile of doxorubicin was calculated by its absorption at 488 nm. The results are shown in FIG. 2B (x axis=time in hours).

Example 4

Determination of Drug Loading

Vesicle containing eluent may be assayed for drug and phospholipids by the following method. Lipid content is estimated by a colorimetric method, (Fiske et al., supra). For high sensitivity measurements of drug content, the sample is passed through HPLC or capillary electrophoresis followed by mass. Total drug incorporated is calculated by first rupturing the vesicles followed by the determination of free drug in solution. Knowing the volume of the vesicle and number of vesicles, the total loading of the drug can be determined. Trapping efficiencies are calculated as the drug/phospholipids ratio after separation of free drug divided by the drug/phospholipids ratio before separation.

Example 5

Characterization of Liposomes/Immunoliposomes

Vesicle size and size distribution may be determined by photon correlation spectroscopy using a Malvern Zetasizer 1000HAS spectrometer (Malvern Instruments, Malvern Wores, UK). The light source is a 10 mW He—Ne laser (633 nm) and the scattered light is measured at a right angle using an avalanche photodiode detector. The instrument is calibrated using Latex beads (100 or 200 nm) in 10 mM NaCl. The solution is filtered using a 0.22 µm syringe filter and degassed prior to the measurements. Since very dilute solutions are used, the values for refractive index and viscosity are set equal to the values of water for the calculations of hydrodynamic diameters. The data is analyzed using the Contin algorithm (Malvern Instruments), which calculates Z-average size and polydispersity. The former is the average hydrodynamic diameter of the vesicles whereas the latter is a measure of the width of the vesicle size distribution.

Example 6

Detection of Liposomes/Immunoliposomes In Vitro and In Vivo

Detection of liposomes/immunoliposomes may be carried out in vitro or in vivo as follows. A water-soluble radiolabel is loaded into the liposomes/immunoliposomes in place of (or along with) drug. Radiotracers such as cholesteryl (4-$^{14}$C) oleate, $^{125}$I-labeled antibody or 111In-DTPA are included in the liposome/immunoliposome formulation to quantify liposome/immunoliposome levels in vitro or in vivo (Ogihara-Umeda, et al. (1996) *J Nucl Med* 37:326-332). Cholesteryl (4-$^{14}$C) oleate is used because it is non-exchangeable between liposomes/immunoliposomes and other membraneous particles. Alternatively, chromophoric elements such as cholesteryl BODIPY 576/589 or carboxyfluorescein 485/535 provide a "built-in" method for monitoring the liposome/immunoliposome localization utilizing fluorescence spectroscopy.

Example 7

Evaluation of the Therapeutic Efficacy of In Vitro Against a Breast Cancer Cell Line Liposomes and immunoliposomes containing anticancer drugs are labeled with different radiolabels, and are then cultured with a Her-2/neu positive human breast cancer cell line (BT474) to test the binding efficiency and the therapeutic efficacy of the delivery systems. The binding efficiency is obtained by comparing radiolabel signals from liposomes with that from immunoliposomes. The therapeutic efficacy obtained from combination therapy is compared with the efficacy achieved with free drugs and each delivery system alone. The double radiolabeled immunoliposomes are cultured with BT474 to study the endocytotic uptake and drug release abilities of immunoliposomes.

Liposome/Immunoliposome Binding and Uptake

Her-2/neu positive BT474 human breast cancer cell line is used as a clinically relevant in vitro model. Following a published approach (Nallamothu, et al. (2006) *AAPS Pharm Sci Tech* 7: E32), fates of immunoliposomes and liposomes are monitored by following the immunoliposomes labeled with $^{125}$I on the antibody component and the liposomes labeled with a radiolabel (such as 111In-DTPA) trapped in the hydrophilic core of the liposomes. BT474 cells in 24-well culture plates are incubated with radiolabeled liposomes and/or immunoliposomes for various incubation times (0-24 hr) after which the cells will be washed to remove unbound material. At the end of incubation time, cell viability is measured. Untreated BT-474 cells or cells treated with free drugs serve as controls. Cells are harvested by mechanical scraping, centrifugation and a subsequent wash of the cell pellet with PBS. The degree of cellular uptake is determined from the ratio of radioactivity in the cell pellet to that in the supernatant (Koning, et al. (1999) *Biochim Biophys Acta* 1420: 153-167). Non-removable label is determined in the cell pellet after treating the cells with acid wash (Geissler, et al. (1992) *Cancer Res* 52: 2907-2915). The radioactivity in cell pellet is normalized for the amount of cellular protein determined by protein assay using BSA standard (Koning, et al. (2002) *Cancer Detect Prev* 26: 299-307).

Double Radiolabeled Experiments

In order to study the uptake and processing of immunoliposomes by cells in more detail, double radio-labeled immunoliposomes is utilized. The fate of the hydrophilic radiolabel loaded into the immunoliposome vesicle $^{111}$In-DTPA is compared with the fate of the radiolabel ($^{125}$I) on the targeting antibody. This provides information on the release of drug payloads into the interior of cells. If the hydrophilic contents of the immunoliposome vesicle are released intracellularly, the $^{111}$In should be retained inside the cell, whereas if the $^{111}$In-DTPA is released outside the cell, it should not enter the cell (Franano, et al. (1994) *Nucl Med Biol* 21: 1023-1034). It is conceivable that the drug payload could be released somewhat extracellularly, prior to the immunoliposomes entering cells by ligand-receptor reaction mediated internalization. The $^{111}$In and $^{125}$I radioactivities can be distinguished by counting separate energy windows or by recounting samples for the longer-lived $^{125}$I after decay of $^{111}$In. Comparing the intracellular counts indicates whether the immunoliposomes retain the contents of the vesicle until they are endocytosed. For these studies, the antibodies are labeled with an $^{125}$I-labeled acylating agent such as N-succinimidyl 4-guanidinomethyl-3-[$^{125}$I]-iodobenzoate. In the event of intracellular degradation of the antibodies during the timeframe of the experiment, the labeled catabolites are charged and therefore will be retained intracellularly (Vaidyanathan, et al. (2001) *Bioconjug Chem* 12: 428-438). These labeling techniques are known in the art. See, e.g. Knight, et al. (1996) *J Nucl Med* 37: 476-482 and Knight, et al. (1998) *Thromb Haemost* 80: 845-851. If instability of the $^{111}$In label presents a problem, a metal chelator such as DOTA is used (Lewis, et al. (1994) *Bioconjug Chem* 5: 565-576; McQuade, et al. (2004) *Bioconjug Chem* 15: 988-996). Fluorescent labeling together with co-focal microscopy is used an alternative to study the internalization of the immunoliposomes into the tumor cells.

Example 8

Evaluation of Biodistribution and Therapeutic Efficacy of Combination Therapy In Vivo Biodistribution and in vivo efficacy of the liposome-based therapeutic compositions is demonstrated in a xenograft tumor mice model. Athymic nude ovariectomized (OVX) mice (simulating post-menopausal breast cancer) (NCI, Frederick, Md.), 4-6 wks old are implanted with BT-474 xenografts supplemented with Estradiol pellets to facilitate tumor growth (Patel, et al. (2007) *Br J Cancer* 96, (8), 1204-15; Baselga, et al. (1998) *Cancer Res* 58(13):2825-31). The mouse is weighed and the tumors are measured every day. The average geometric volume of the tumors is estimated as a spherical object with a metric caliper. Once tumor xenografts become established and 150 to 400 mm$^3$ in volume, mice are randomly assigned to treatment groups.

Liposomes and immunoliposomes containing anticancer drugs are injected intravenously into the mice. The results obtained from the combination therapy are compared with those obtained using each delivery system alone. Treatment is initiated when tumors reach a geometric mean volume of 0.4-0.7 mm$^3$ (small) or 0.8-1.1 mm$^3$ (large). Tumor size and growth delay for a treatment is assessed by the difference in time it takes for a treated tumor to reach the same volume as that of a control; this assessment is continued for up to 2 months post treatment or until tumor weight reaches 10% of body weight, at which time the animal must be sacrificed. Pathological changes in tumors and in normal tissue of treated animals is independently evaluated The liposomes/immunoliposomes may contain a reporter functionality. The reporter functionality may comprise be a fluorescent tag, a radionuclide tag, or other tag. Biodistribution of fluorescence-tagged immunoliposomes is quantified using non-invasive and real time in vivo fluorescence imaging.

For example, biodistribution studies are performed in mice bearing BT-474 xenografts and compared to non-tumor-bearing mice. The presence of Cy5.5 imaging agent in the delivery system allow real-time monitoring and quantitation of fluorescence. Liposome formulations are administered via the lateral tail vein and imaged at different time points (0-48 hr) using an IVIS 50 System (Xenogen Corporation). Fluorescence from Cy5.5 are detected at Ex/Em 745/820 nm, 4 sec exposure time). Tumor and other organ (liver, kidney and heart) accumulation is quantified from fluorescence counts in regions of interest. If tumor accumulation is observed, select mice at that time point are anesthetized (Ketamine/Xylazine) and blood samples are collected from tail incision and weighed. Then 5 ml of saline is injected into the left ventricle and right ventricle is cut to flush out the remaining blood from the organs. Brain, heart, kidney, liver, lung, spleen, eyes and tumors, as well as skin and normal muscle adjacent to the tumor, are removed and weighed and monitored by fluorescence and confocal microscopy.

Radiolabeling to Validate the Biodistribution Study Using Fluorescence Labeling

As an alternative to fluorescence labeling, radiolabeled compound that is encapsulated in the vesicles (both liposomes and immunoliposomes) is used to determine the fate of the delivery system in vivo. These techniques are well established. See, e.g. Nallamothu, et al. (2006) *AAPS Pharm Sci Tech* 7: E32; Knight, et al. (1996) *J Nucl Med* 37: 476-482; Knight L C, et al. (1998) *Thromb Haemost* 80: 845-851, McQuade, et al. (2004) *Bioconjug Chem* 15: 988-996; Knight, et al. (1987) *Biochim Biophys Acta* 924: 45-53; Knight, et al. (1988) *J Nucl Med* 29: 494-502; McQuade, et al. (2003) *Q J Nucl Med* 47: 209-220; Nallamothu, et al. (2006) *PDA J Pharm Sci Tech* 60: 144-155.

Animals are weighed and radiolabeled delivery system is intravenously injected into each animal. At appropriate time post-injection (determined by the fluorescence study, above) animals are euthanized; tumor tissue and the organs are collected. Samples from each tissue are placed in a counting vial and weighed. All samples are counted in a Wallac Wizard gamma counter along with a standard of the administered dose. Concentration of liposomes/immunoliposomes in each tissue can be expressed as a percentage of the administered dose.

The disclosures of each and every patent, patent application, publication and GenBank record cited herein are hereby incorporated herein by reference in their entirety.

One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed is:

1. A composition for treating cancer comprising targeted liposomes comprising a chemotherapy agent and a sensitizer for the chemotherapy agent, and non-targeted liposomes comprising an anti-angiogenic agent, wherein:

said targeted liposomes are immunoliposomes that bind to Her-2/neu;

said chemotherapy agent is doxorubicin, carboplatin, cisplatin, cyclophosphamide, docetaxel, erlotinib, etoposide, fluorouracil, gemcitabine, imatinib mesylate, irinotecan, methotrexate, paclitaxel, sorafinib, sunitinib, topotecan, vincristine or vinblastine;

said sensitizer is verapamil; and said anti-angiogenic agent is bevacizumab.

2. The composition of claim 1 wherein said targeted liposomes comprise hydrogenated soy L-α-phosphatidylcholine (HSPC), cholesterol, 1,2-distearoyl-sn-glycero-3-phosphoethanolamine-N-[(polyethylene glycol)2000] (DSPE-PEG2000) and DSPE-PEG-maleimide.

3. The composition of claim 1 wherein said targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

4. The composition of claim 1 wherein said non-targeted liposomes comprise hydrogenated soy L-α-phosphatidylcholine (HSPC), cholesterol, 1,2-distearoyl-sn-glycero-3-phosphoethanolamine-N-[(polyethylene glycol)2000] (DSPE-PEG2000) and DSPE-PEG-maleimide.

5. The composition of claim 4 wherein said non-targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

6. The composition of claim 1 wherein said non-targeted liposomes are conjugated to polyethylene glycol.

7. The composition of claim 1 wherein the chemotherapeutic agent is doxorubicin.

8. A method for treating cancer comprising administering to a subject in need of such treatment targeted liposomes comprising a chemotherapy agent and a sensitizer for the chemotherapy agent, and non-targeted liposomes comprising an anti-angiogenic agent wherein:
said targeted liposomes are immunoliposomes that bind to Her-2/neu;
said chemotherapy agent is doxorubicin, carboplatin, cisplatin, cyclophosphamide, docetaxel, erlotinib, etoposide, fluorouracil, gemcitabine, imatinib mesylate, irinotecan, methotrexate, paclitaxel, sorafinib, sunitinib, topotecan, vincristine or vinblastine;
said sensitizer is verapamil;
said anti-angiogenic agent is bevacizumab; and
said cancer is breast cancer, cardiac cancer, lung cancer, gastrointestinal cancer, genitourinary tract cancer, liver cancer, bone cancer, nervous system cancer, gynecological cancer, hematologic cancer, skin cancer or adrenal gland cancer.

9. The method of claim 8 wherein said targeted liposomes comprise hydrogenated soy L-α-phosphatidylcholine (HSPC), cholesterol, 1,2-distearoyl-sn-glycero-3-phosphoethanolamine-N-[(polyethylene glycol)2000] (DSPE-PEG2000) and DSPE-PEG-maleimide.

10. The method of claim 8 wherein said targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

11. The method of claim 8 wherein said non-targeted liposomes comprise hydrogenated soy L-α-phosphatidylcholine (HSPC), cholesterol, 1,2-distearoyl-sn-glycero-3-phosphoethanolamine-N-[(polyethylene glycol)2000] (DSPE-PEG2000) and DSPE-PEG-maleimide.

12. The method of claim 8 wherein said non-targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

13. The method of claim 8 wherein said non-targeted liposomes are conjugated to polyethylene glycol.

14. The method according to claim 8, wherein the chemotherapeutic agent is doxorubicin.

15. The method of claim 8 wherein said targeted liposomes are administered to said subject at the same time as said non-targeted liposomes.

16. The method of claim 8 wherein said targeted liposomes are administered to said subject prior to the administration of said non-targeted liposomes.

17. The method of claim 8 wherein said targeted liposomes are administered to said subject subsequent to the administration of said non-targeted liposomes.

18. The method of claim 8 wherein said cancer is breast cancer.

19. The method of claim 14, wherein said cancer is breast cancer.

20. A kit comprising, in a first compartment, a composition comprising targeted liposomes comprising a chemotherapy agent and a sensitizer for the chemotherapy agent, and, in a second compartment, a composition comprising non-targeted liposomes comprising an anti-angiogenic agent, wherein:
said targeted liposomes are immunoliposomes that bind to Her-2/neu;
said chemotherapy agent is doxorubicin, carboplatin, cisplatin, cyclophosphamide, docetaxel, erlotinib, etoposide, fluorouracil, gemcitabine, imatinib mesylate, irinotecan, methotrexate, paclitaxel, sorafinib, sunitinib, topotecan, vincristine or vinblastine;
said sensitizer is verapamil; and
said anti-angiogenic agent is bevacizumab.

21. The kit of claim 20 wherein said targeted liposomes comprise hydrogenated soy L-α-phosphatidylcholine (HSPC), cholesterol, 1,2-distearoyl-sn-glycero-3-phosphoethanolamine-N-[(polyethylene glycol)2000] (DSPE-PEG2000) and DSPE-PEG-maleimide.

22. The kit of claim 20 wherein said targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

23. The kit of claim 20 wherein said non-targeted liposomes comprise hydrogenated soy L-α-phosphatidylcholine (HSPC), cholesterol, 1,2-distearoyl-sn-glycero-3-phosphoethanolamine-N-[(polyethylene glycol)2000] (DSPE-PEG2000) and DSPE-PEG-maleimide.

24. The kit of claim 23 wherein said non-targeted liposomes comprise about 50 mole % hydrogenated soy L-α-phosphatidylcholine (HSPC), about 45 mole % cholesterol, about 3 mole % 1,2-distearoyl-sn-glycero-3-phosphoethanolamine-N-[(polyethylene glycol)2000] (DSPE-PEG2000) and about 2 mole % DSPE-PEG-maleimide.

25. The kit of claim 20 wherein said non-targeted liposomes are conjugated to polyethylene glycol.

26. The kit according to claim 20 wherein the chemotherapeutic agent is doxorubicin.

* * * * *